United States Patent [19]

Winchell

[11] 4,079,124
[45] Mar. 14, 1978

[54] METHOD OF PREPARING X-RAY CONTRAST MEDIA CONTAINING ORES OF HAFNIUM, TANTALUM AND TUNGSTEN

[75] Inventor: Harry S. Winchell, Lafayette, Calif.

[73] Assignee: Medi-Physics, Inc., Emeryville, Calif.

[21] Appl. No.: 678,787

[22] Filed: Apr. 21, 1976

[51] Int. Cl.$^2$ ............................................. A61K 29/02
[52] U.S. Cl. ........................................ 424/4; 424/127; 424/131
[58] Field of Search ............................ 424/4, 127, 131

[56] References Cited

U.S. PATENT DOCUMENTS

| 2,461,702 | 2/1949 | Slaybaugh | 424/4 |
|---|---|---|---|
| 3,542,915 | 11/1970 | Bodkin | 424/4 |
| 3,592,185 | 7/1971 | Frei et al. | 424/4 X |
| 3,937,800 | 2/1976 | Dure-Smith et al. | 424/4 |

FOREIGN PATENT DOCUMENTS

| 2891/64 | 3/1964 | Japan | 424/4 |
|---|---|---|---|
| 1,174,031 | 12/1969 | United Kingdom | 424/4 |

OTHER PUBLICATIONS

Hackh's Chemical Dictionary, The Bladiston Co., 3rd Ed., Philadelphia, (1944), pp. 216, 758, 831, 874 and 875.

*Primary Examiner*—Albert T. Meyers
*Assistant Examiner*—Vera C. Clarke
*Attorney, Agent, or Firm*—Samuel L. Welt; Bernard S. Leon; R. Hain Swope

[57] ABSTRACT

A method of preparing enteric X-ray contrast media particularly suited to the use of high energy X-ray sources are disclosed. The disclosed media comprise hafnium, tantalum, tungsten, oxides or insoluble salts thereof in purified form, mixtures thereof and, more particularly, partially purified ores containing one or more of them in combination with a suitable carrier.

3 Claims, No Drawings

METHOD OF PREPARING X-RAY CONTRAST MEDIA CONTAINING ORES OF HAFNIUM, TANTALUM AND TUNGSTEN

BACKGROUND OF THE INVENTION

Radiopaque materials utilized today are generally of two types, viz., barium sulfate preparations and preparations containing iodinated organic compounds. The first of these types of preparations, i.e. preparations containing barium sulfate, suffer a number of disadvantages most of which are related to difficulty in obtaining a stable, high density, homogeneous suspension of the extremely insoluble barium sulfate and causing such suspensions to adhere to the intestinal mucosa. Even if such problems were to be overcome by the discovery of an ideal vehicle for barium sulfate, the resulting preparations would still not be amenable to the use of high energy X-rays. It is recognized that the use of high energy X-rays results in a decrease in the radiation dose absorbed by the body relative to the amount of information-bearing X-rays which reach the radiation detector system. It is also recognized in the art of radiopaque preparations that, as the energy level of X-rays utilized increases above the K-absorption edge of barium, the relative absorption of barium and its salts decreases. The same is true for the organic iodine preparations.

The fact that barium sulfate and the iodine preparations are optimally suited for use with medium energy X-rays and are inefficient in absorbing high energy X-rays whose energy significantly exceeds their K-absorption edge is of critical importance to the patient. The type of studies contemplated with such preparations, particularly the barium sulfate preparations, require the use of not only a large quantity of the preparation itself but also, because of their X-ray absorption properties, a very large dose of radiation. This is unfortunate but necessary to obtain satisfactory diagnostic information, e.g. when conducting a gastrointestinal tract study. It has been long established that the higher the energy level of radiation passing through the human body the less energy is absorbed thereby. Therefore, it is readily apparent that X-ray contrast preparations which are optimally suited for use with high energy X-rays would be highly advantageous in comparison with the barium sulfate and iodinated preparations in terms of the amount of radiation absorbed by the patient. Such preparations are provided by the present invention.

DETAILED DESCRIPTION OF THE INVENTION

In accordance with the present invention, compositions are provided which are well suited for contrast media diagnostic procedures. The compositions of the present invention utilize high energy X-rays which can be generated utilizing conventional equipment commonly utilized in X-ray laboratories, hospitals and the like. The preparations of the present invention comprise one or a mixture of high Z elements tantalum, tungsten and hafnium, purified insoluble salts or oxides thereof or a partially purified ore containing one or more of them in a suitable liquid carrier. Wherein the preparations of the invention comprise an ore containing one or a mixture of tantalum, tungsten or hafnium in a suitable liquid carrier, said ore is in a partially purified state. The partial purification comprises comminuting the ores to a fine particulate state and then treating the particles to remove soluble matter therefrom.

The fact that the compositions of the present invention are suitable to be used with high-energy X-rays makes them advantageous over similar preparations which are used with medium- or low-energy Z-rays. An advantage of 65–70 KeV X-rays, which correspond to the K-absorption edge of hafnium, tantalum and tungsten, is that they produce sharper X-ray images because of a significantly low probability of scatter in the low-Z elements of the body.

Additionally, the use of such higher X-ray energies results in a higher contrast between the radiographic agent and tissue than with medium- or low-energy X-rays. High energy X-rays also show less contrast between bone and soft tissue than lower energy X-rays. Since boney background is known to interfere with imaging of radiographic agents which use medium- or low-energy X-rays, a sharper contrast is realized in accordance with the present invention due to the use of high energy X-rays.

Also, a marked improvement in contrast enhancement is possible utilizing high-energy X-rays and high-Z radiographics by the use of double-exposure image subtraction techniques. This method takes advantage of the fact that the effective absorption coefficient of tissue and bone are essentially the same for X-rays just below and just above the 65–70 keV K-absorption edge for hafnium, tantalum and tungsten. Therefore, subtraction of an image obtained using X-rays of principal energy slightly below 65 keV from an image obtained using X-rays of principal energy at or slightly above the 65–70 keV range should result in marked enhancement of the image cast by the high-Z radiographic agent.

Of the high-Z, i.e., high atomic number, elements utilized in the present invention only tantalum has been previously utilized for diagnostic procedures. In such use, pure tantalum as a very fine powder is inhaled without a carrier for bronchiography. Further, U.S. Pat. No. 3,937,800 discloses a composition for bronchiography comprising finely divided tantalum and a metallic soap in an oily vehicle. Such use is, in part, limited by the fact that pure tantalum is a very expensive material.

The fact that the elements of the present invention are expensive in their pure form can be a drawback to their widespread use in radiopaque formulations since a large quantity, e.g. 200 to 250 grams of material, may be required to conduct a single enteric study. Therefore, it is preferred in accordance with the present invention to utilize ores containing one or more of the high-Z elements named herein in insoluble form, e.g., oxides and-/or insoluble salts which ores have been comminuted to a fine particulate state and treated to remove soluble material.

Tantalum, hafnium and tungsten are principally present in their ores as simple or complex oxides. They may also be present to a much lesser degree as silicates, borates or complexes thereof with oxides. Depending on the extraction and purification process utilized, tantalum, hafnium and tungsten may variously be produced in a purified form as the free metal, oxides, e.g. tantalum pentoxide or, less frequently, in the form of insoluble salts, e.g., hafnium nitride, tungsten carbide and the like. The terminology "purified oxides and insoluble salts" as utilized herein refers to such compounds.

Among the contrast media utilized in accordance with the present invention, the partially purified ores of tantalum, hafnium and tungsten are preferred. The ores are preferred because they are only partially purified and the elements therein are not isolated, thus they are substantially less expensive to the patient than the pure elements and are equally effective. For example, the cost of tantalite, an ore containing tantalum which will be discussed hereinafter, is approximately 1/6 that of the same quantity of pure tantalum. The relative cost of other ores to be discussed thereinafter will vary in comparison with the pure elements. In addition, the ores are preferred for use in this invention because a mixture of elements is present, thus the preparation containing them will absorb a wider range of radiation therefore allowing for use of a broader band of X-ray energies that that which would be optimal for use with a radiopaque agent consisting of a single element.

The ores useful in accordance with the present invention are those which contain at least one of the elements hafnium, tantalum or tungsten. For example, among the principal tantalum-containing ores, many of which usually also contain niobium (columbium), are columbite, tantalite, loparite, fergusonite and the like. Other elements which are often found in these ores include titanium, tin and iron. The elements are usually present in these ores as the oxide, multiple oxides and hydroxide. The two principal ores containing hafnium are zircon and baddeleyite, both of which contain hafnium in a ratio of at least 1:50 with zirconium wherein both are present as the oxide. Principal ores containing tungsten include huebnerite, wolframite, ferberite, scheelite and powellite. Preferred ores in accordance with the present invention are tantalite, columbite and scheelite. It is also preferred to mix two or more of the above named ores to achieve a wider range of absorbtion of high energy X-rays or to mix a small quantity of a particular element with an ore containing one of the others. A preferred combination of this type is scheelite with added tantalite.

As stated above, the ores utilized in the preferred compositions of the present invention are prepared for use by a simple process which makes their use for radiographic procedures economically attractive. Initially, the ores are comminuted to a fine particle size, i.e. the majority of particles are substantially no larger than one micron in diameter. After the ore has been reduced to the proper particle size, the particles are then extracted by washing with aqueous solutions containing solutes comparable to those formed in the human gastrointestinal tract. The washing procedure would, for example, be initially with an acidic solution to similate conditions in the stomach and thereafter with an alkaline solution to simulate conditions in the gut. The washing solutions may additionally contain enzymes such as are found in the gastrointestinal tract. Several washings are required and it is also preferred that the solutions are heated, e.g. to a temperature of at least 90° C. The washing operation is intended to purify the ore in the sense that any soluble salts or other materials are removed thereby thus preventing their absorbtion into the body. The result of the grinding and washing procedures is a fine granular powder which, in a suitable carrier, is capable of forming a film on intestinal mucosal surfaces. The powder produced from tantalum, hafnium or tungsten-containing ores in accordance with the invention absorbs high energy X-rays and is not absorbed into the body. This powder is then incorporated into a suitable contrast media carrier therefor.

The carriers for the contrast media in accordance with the present invention are pharmaceutically acceptable viscous liquids. Preferred liquids include propylene glycol, glycerin and some vegetable oils, e.g. peanut oil, safflower oil, cotton seed oil and the like. Where the viscosity of the liquid carriers is not sufficient to suspend the contrast agents, pharmaceutically acceptable thickening and/or suspending agents may be added to adjust the viscosity to the required level. Examples of suitable agents include polyvinylpyrrolidone, carboxymethylcellulose, lecithin, acacia and the like. The amount of contrast agent incorporated in the carrier is not particularly critical. Usually, however, the preparations in accordance with the invention contain from about 10% by weight to about 50% by weight of hafnium, tantalum or tungsten and/or their ores. The amount of the contrast media present in the final preparations as well as the viscosity thereof will vary considerably with the type of study being conducted and the mode of administration intended. For example, if the preparation is to be infused into a body cavity, it must be sufficiently fluid to be withdrawn into a syringe and easily installed into the cavity. The viscosities required for particular studies are recognized in the art. Therefore, the amounts of thickening or suspending agent to be incorporated within the formulations as disclosed herein to achieve the desired viscosities are considered to be within the skill of the art.

The preparations of the present invention may additionally contain other ingredients such as are recognized as being conventional in such preparations, e.g. flavoring agents wherein such preparations are intended to be orally ingested for studies of the upper gastrointestinal tract, preservatives and the like. The incorporation of hafnium, tantalum, tungsten, their purified insoluble salts or oxides or their ores into the carrier material is carried out by techniques conventional in the art, preferably wet granulation.

The radio contrast preparations in accordance with the present invention have been found to exhibit good adherence properties. Such properties are essential since the preparation must effectively coat the walls of the organ to be studied in order to yield a good picture. Further, the preparations of the invention are suited for use with conventional X-ray equipment since such equipment can be modified with conventional filters so that all but the high energy X-rays suitable for the intended study are filtered. The X-ray energy may be precisely filtered so that the mean X-ray energy approximates the K-absorption of a pure element or filtered to block only low and medium energy X-rays wherein an ore is utilized.

The following examples further illustrate the invention.

EXAMPLE 1

Utilizing a conventional diagnostic X-ray machine equipped with aluminum and copper absorbers, samples of the material to be tested were placed in the midplane of a plexiglass phantom intended to approximate in vivo conditions under which such agents would be used. Conventional thermo-luminescent dosimeters were utilized to evaluate absorbed radiation dose front, mid and back plane of the phantom. Various levels of X-rays were passed through the phantom. All exposures were adjusted to yield comparable background density on the X-ray film therefor. The comparison made on the basis of absorbed radiation dose reasonably approximates the reduction in radiation dose expected in the clinical situation utilizing the stated operating conditions. For this experiment barium was in the form of barium sulfate, tantalum, hafnium and tungsten were utilized as oxides and iodine was in the form of sodium iodate. All substances were ground and passed through a U.S. Standard 250 mesh screen.

The results of this experiment are given in the following table. In the table, section A represents operating parameters of the operating machine (kvp, in A, exposure time and filtration). Section B contains the absorbtion data in mR for exposure at the upper surface (front) midplane and lower surface (back) of the phantom. Section C gives the effective mass absorption coefficient ($\lambda$) expressed as # per gram of the element /cm$^2$ and the correlation coefficient ($r$) of the data to the regression line utilized in the determination of $\lambda$.

the oxides of tantalum, hafnium and tungsten have effective linear absorption coefficients two or three times greater than that of barium sulfate. This is due largely to the greater effective density of the metal oxides powders than that of barium sulfate powder of comparable particle size. This difference is accentuated with the use of "hard" X-rays (125 kvp, 5 mm Al, and 3.2 mm Cu extrinsic filtration) where powdered hafnium and tantalum oxides have linear absorption coefficients of over seven times that of powdered barium sulfate. This data indicates that with the use of such "hard" X-rays, a layer of hafnium or tantalum oxides on the intestinal mucosa one-seventh the thickness of a layer of barium sulfate would yield comparable density on the X-ray film. Conversely, wherein the layers of contrast media on the intestinal mucosa are of comparable thickness, significantly greater contrast will be obtained during radiography with the use of hafnium, tungsten or tantalum oxides than with barium sulfate.

TABLE

| A: X-RAY MACHINE OPERATING CONDITIONS | | | | | |
|---|---|---|---|---|---|
| Voltage (kvp) | 85 | 125 | 125 | 125 | 125 |
| Current (mA) | 132 | 64 | 162 | 320 | 160 |
| Exposure Time (sec) | 1/2 | 1/29 | 1/30 | 1/5 | 2.5 |
| mA × Exposure time (in secs) | 11 mAs | 3.2 mAs | 6.4 mAs | 64 mAs | 400 mAs |
| Filtration used | none | none | 5mm Al | 5mm Al 3.2mm Cu | 5mm Al 6.4 mm Cu |
| B: ABSORBED IN mR IN PHANTOM PER EXPOSURE TO YIELD CONSTANT BACKGROUND FILM DENSITY | | | | | |
| Upper surface | 62.4 ± 6.2 | 32.3 ± 3.2 | 20.4 ± 2.0 | 10.8 ± 1.1 | 9.6 ± 1.0 |
| Midplane | 16.3 ± 1.6 | 11.7 ± 1.2 | 10.1 ± 1.0 | 6.9 ± 0.7 | 5.7 ± 0.7 |
| Lower surface | 4.4 ± 0.7 | 3.7 ± 0.7 | 3.9 ± 0.7 | 3.3 ± 0.7 | 2.4 ± 0.7 |
| C: EFFECTIVE ABSORPTION COEFFICIENT $\lambda$ (# PER GRAM OF ELEMENT/cm$^2$) OVER CORRELATION COEFFICIENT ($r$) | | | | | |
| Iodine | 4.78/.96 | 4.91/.97 | 4.51/.93 | 3.73/.96 | 2.87/.98 |
| Barium | 4.96/.98 | 5.59/.99 | 4.46/.98 | 3.34/.99 | 2.77/.96 |
| Hafnium | 3.35/.95 | 4.06/.98 | 4.48/.98 | 6.05/.93 | 5.19/.99 |
| Tantalum | 3.14/.97 | 3.92/.98 | 4.04/.98 | 6.68/.97 | 5.79/.99 |
| Tungsten | 3.33/.95 | 3.45/.94 | 3.75/.92 | 4.46/.86 | 5.65/.94 |

It is readily appreciated from an examination of the data in the above table that, as the voltage on the X-ray machine is increased and the filtration utilized to allow only high energy or "hard" X-rays to pass, the absorbed radiation dose sharply decreases, i.e., on the upper surface from 62.4 mR to 9.6 mR, midplane from 16.3 mR to 5.7mR and lower surface from 4.4 mR to 2.4 mR. Utilizing "soft" X-rays, i.e. 85 kvp with no extrinsic filtration, iodine and barium have effective mass absorbtion coefficients approximately 50% greater than the other three elements tested while the opposite is true with the high energy or "hard" X-rays. From this data it can be appreciated that patients would receive considerably more radiation dose using barium sulfate and "soft" X-rays in comparison with a comparable weight of tantalum, hafnium or tungsten and "hard" X-rays.

Even more meaningful for evaluating the relative merits of agents to be used for enteric studies than the comparison of effective element mass absorption coefficients given in the table is the comparison of linear effective absorption coefficient (#/cm) of the powdered agents. Such a comparison is important because it is the X-ray absorption of the layer of radiographic material on the surface of the intestinal mucosa which determines image contrast.

Such an analysis was performed based on the measured weight per unit volume of lightly packed powders of each of the above materials with the exception of sodium iodate. All powders were hand ground and passed through a 250-mesh screen. It was found that even with "soft" X-rays (85 kvp, no extrinsic filtration),

EXAMPLE 2

A sample of Ta-177 pentoxide was combined with carrier Ta$_2$O$_5$, and formed into separate fluid suspensions in each of water, glycerin and vegetable oil, respectively. All suspensions were orally administered to rats. None showed evidence of appreciate systemic absorption. Tantalum pentoxide was found to form excellent homogeneous pastes in glycerin, propylene glycol and vegetable oil at concentrations of 10, 40 and 80% by weight. These pastes retained much of their wetting properties even with the addition of water. Pastes obtained with the oxides of tungsten and hafnium as well as finely ground tantalite produced comparable results. The viscosity of the 10% by weight suspensions in propylene glycol was significantly increased by the addition of 10% weight to volume of polyvinylpyrrolidone. These suspensions retained good wetting properties and exhibited marked improvement in settling of the metal oxide powders.

I claim:

1. A method of preparing an X-ray contrast medium which comprises communiting one or more ores containing insoluble oxides or salts of tantalum, hafnium or tungsten to a fine powder, partially purifying said powder by washing same with aqueous solutions containing solutes comparable to those usually found in the human gastrointestinal tract thereby removing therefrom constituents soluble in said solutions and combining the resultant powder with a suitable viscous liquid carrier.

2. The method in accordance with claim 1 wherein said partially purified ore is homogeneously mixed with one or more purified substances selected from the group consisting of tantalum, hafnium, tungsten, oxides thereof and insoluble salts thereof before being combined with said carrier.

3. The method in accordance with claim 1 wherein said ore is selected from the group consisting of tantalite, columbite and scheelite.

* * * * *